United States Patent [19]

Domb

[11] Patent Number: 4,999,417

[45] Date of Patent: Mar. 12, 1991

[54] BIODEGRADABLE POLYMER COMPOSITIONS

[75] Inventor: Abraham J. Domb, Baltimore, Md.

[73] Assignee: Nova Pharmaceutical Corporation, Baltimore, Md.

[21] Appl. No.: 330,588

[22] Filed: Mar. 30, 1989

[51] Int. Cl.$^5$ .......................................... C08G 67/04
[52] U.S. Cl. .................................. 528/271; 528/272; 528/310; 524/17; 524/21; 524/599; 424/78; 424/409; 424/426; 424/428
[58] Field of Search ....................... 528/271, 272, 310; 524/17, 21, 599; 424/78, 426, 428, 409

[56] References Cited

U.S. PATENT DOCUMENTS 4,757,128 7/1988 Domb et al. .......................... 528/271
4,789,724 12/1988 Domb et al. .......................... 528/176

OTHER PUBLICATIONS

*Ency. of Poly. Sci. & Tech.*, 10:630–653, Wiley (1969).
Domb et al., *Macromolecules*, 21(7):1925–1929 (1925).
Domb et al., *J. of Polymer Sci: Part A: Polymer Chemistry*, 25:1–12 (1987).
Leong et al., *J. of Biomedical Materials Research*, 19:941–955 (1985).
Gonzalez et al, *Die Angewandte Makromolekulare Chemie*, 55:85–96 (1976).

Primary Examiner—John Kight, III
Assistant Examiner—Sam A. Acquah
Attorney, Agent, or Firm—Cushman, Darby & Cushman

[57] ABSTRACT

Biodegradable polyanhydrides or polyester compositions based on amino acids. The compositions may be used as carriers for drugs or the like or as the drug source itself. The polymers are prepared from amino acids which are modified to include an additional carboxylic acid group.

19 Claims, No Drawings

BIODEGRADABLE POLYMER COMPOSITIONS

This invention relates to biodegradable polymer compositions derived from amino acids. These polymers may be used as carriers for the release of active agents, e.g. drugs. They may also be made from bioactive amino acids so that the polymers themselves or degradation products thereof are bioactive.

BACKGROUND OF THE INVENTION

A great deal of research has been directed in recent years to developing biodegradable polymer compositions for use in providing the controlled delivery of biologically active agents, particularly drugs. Such compositions may be implanted into a patient and function to dispense the active agent at a controlled rate sufficient to provide the dosage required for treatment.

Biodegradable polymer compositions release the active agent as the polymer is eroded away by the environment through dissolution hydrolysis processes or enzymatic degradation. When such polymers are used for delivery of drugs within medical applications, it is essential that the polymers themselves be non-toxic and that they degrade into non-toxic degradation products as the polymer is eroded by body fluid.

In order to minimize the toxicity of the intact polymer carrier and its degradation products, polymers have been designed based upon naturally occurring metabolites. The most extensively studied examples of such polymers are the polyesters derived from lactic or glycolic acid [D. L. Wise et al., Drug Carriers in Biology and Medicine, G. Gregoriadis ed., Academic Press, London, 1979, pp. 237-270 and polyamides derived from amino acids D.A. Wood, *Int. J. Pharm.* 7:1, 1980].

Toxicity of the polymer and its degradation products represents only one of a number of factors which need to be considered in order to provide an effective biodegradable polymer composition for use in the controlled delivery of a drug or other active agent. Thus, the polymer composition must also have suitable physical and mechanical properties including effective surface erosion so that the active agent is released in a controlled manner. Bulk erosion is not satisfactory because this results in a complete breakup of the polymer composition rather than providing a slow or controlled release of the active agent. Bulk erosion usually occurs when the polymer is hydrophilic and absorbs water to the point of becoming sponge-like. Many polymer compositions cannot be effectively used as controlled release biodegradable polymers because they are hydrophilic and undergo bulk erosion. Typical of such polymers are polylactic acid or polyglutamic acid.

Despite the extensive research activity in this field, only a relatively few bioerodible polymer compositions have been developed for in vivo use. Examples of useful compositions are described in U.S. Pat. No. 4,070,347 which discloses polycarbonate and polyorthoester polymeric compositions. Polylactic acid and lactic/glycolic acid copolymers have also been employed for controlled release of biologically active substances. These materials, however, suffer from the problem of bulk erosion referred to earlier.

In recent years a new class of biodegradable polymers, the polyanhydrides, has been introduced for medical use. These polymers display superior physical and mechanical properties with respect to erodible carriers for controlled release drug delivery systems (Rosen, H.B., Chang, J., Wnek, G.E., Linhardt, R.J., and Langer R., *Biomaterials,* 4 131, 1983; Leong, K.W., Brott, B.C. and Langer R., *J. Biomed. Mat. Res.,* 19, 941, 1985; Mathiowitz, E., Saltzman, W.M., Domb, A.J., Dor Ph., Langer, R., *J. Appl. Polym. Sci.,* 35, 755, 1987). See also Domb, A. J., Ron, E. and Langer, R., *Macromolecules,* 1988, 21, 1925 and Domb et al, U.S. Pat. Nos. 4,757,128 and 4,789,724.

Notwithstanding the foregoing efforts, there is still considerable room for improvement in biodegradable polymer compositions for use in providing for the controlled release of drugs or the like. Accordingly, the principal object of the invention is to provide such improvements.

A more specific object is to provide biodegradable polymers based on naturally occurring amino acids. An additional object includes the provision of biodegradable polymer compositions based on amino acid derivatives which are useful as carriers for the controlled release of drugs or other active agents. A further object is to provide biodegradable polymers which have improved physical and mechanical properties. Another important object is to provide biodegradable polymers based on bioactive amino acids whereby the polymers themselves or the degradation products thereof can effectively function as the controlled release drug or other active agent. Other objects will also be hereinafter apparent.

Amino acids are the main metabolites of the body. Accordingly, polymers based on amino acids which degrade into their amino acid counterparts offer the possibility of favorable surface and erosion biocompatibility. In addition, polymers with alternating amide, imide, azo, urethane, urea or thiourea bonds and anhydride or ester bonds in the polymer backbone as contemplated herein, have improved physical and mechanical properties as a result of the incorporation of bonds with high cohesion energy.

Another important advantage of forming amino acids into biodegradable polymers is the fact that many amino acids are biologically active and are used as drugs in the clinic. Degradable polymeric drugs, releasing pharmacologically active amino acids in a controlled fashion for extended periods of time, improve therapy effectiveness and bioavailability of the drug ('Design of Prodrugs', Bundgaard H. editor, Elsevier Sci. Pub., Amsterdam, 1985).

Examples of amino acid drugs suitable for the polymeric drug approach contemplated herein include biologically active natural α-amino acids, e.g., glycine, γ-amino butyric acid (as brain transmitters); phenylalanine derivatives i.e. L-dopa, D-thyroxine; aminosalicylic acid derivatives; tyrosine derivatives (as adjuvants); β-lactam antibiotics, such as ampicillin and cephalexin, and oligopeptides (as peptidic hormones) with carboxylic acid and amino group terminals, i.e. L-alanyl-DL-alanine, L-alanyl-L-alanyl-L-alanyl-L-alanine, and alanyl-leucyl-alanyl-leucine.

SUMMARY OF THE INVENTION

The present invention comprises a variety of biodegradable polymeric compositions formed of modified amino acid monomers, which can be polymerized by a hydrolytically labile anhydride or ester bond. The amino acid monomers are modified at the amino group so as to provide on polymerization, polyanhydrides or polyesters which include amide, imide, urethane, azo, urea or thiourea bonds with the amino nitrogen in the polymer backbone. The resulting polymer compositions display the properties essential for effective use as, for example, carriers for the controlled release of drugs or other active agents. The indicated amide, imide, azo, urethane, urea or thiourea groups in the polymer backbone provide high cohesion energy and thus result in polyanhydrides or polyesters which have physical and mechanical properties that make the polymers highly desirable for biodegradable uses including biodegradable polymeric drugs based on biologically active amino acids.

The polyanhydrides previously proposed for use as drug carriers were prepared by melt or solution polymerization of monomers having two carboxylic acid groups. See Domb et al., *Journal of Polymer Science*, Part A, Polymer Chemistry 1987, Vol. 25, 3373; and the other references earlier noted, e.g., Domb et al., *Macromolecules*, 1988, 21, 1925; and U.S. Pat. Nos. 4,757,128 and 4,789,724. Amino acids, however, have one carboxylic acid and one amine group which is suitable for polyamide (polypeptide) formation, not for polyanhydrides or polyesters. Accordingly, in the present invention, the amino acids are first converted to dicarboxylic acids either by coupling the amino acid with another molecule having a carboxylic acid group, or by the coupling of two amino acids, via the amino group. These amino acids are then polymerized, with or without other monomers, to provide the biodegradable polymer compositions of the invention.

The invention contemplates the following types of polymers:

a. Polymers of diacids made by coupling the amino acid with another molecule having a carboxylic acid group and characterized by the recurring unit:

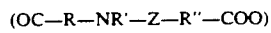
(OC—R—NR'—Z—R"—COO)

b. Polymers of diacids made by coupling of two amino acids, using a coupling agent, and characterized by the recurring unit:

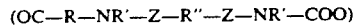
(OC—R—NR'—Z—R"—Z—NR'—COO)

c. Polymers of diacids made by direct coupling of two amino acids, by an azo, urea or thiourea bond, and characterized by the recurring unit:

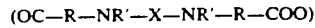
(OC—R—NR'—X—NR'—R—COO)

d. Polymers of at least one dicarboxylic acid made by coupling an amino acid with another molecule having a carboxylic acid group, and at least one glycol, the polymer being characterized by the recurring unit:

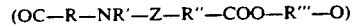
(OC—R—NR'—Z—R"—COO—R'"—O)

e. Polymers of at least one diacid made by coupling of two amino acids using a coupling agent, and at least one glycol, the polymer being characterized by the recurring unit:

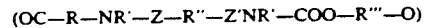
(OC—R—NR'—Z—R"—Z'NR'—COO—R'"—O)

and, f. Polymers of at least one diacid made by direct coupling of two amino acids, by an azo urea or thiorea bond, at least one glycol, the polymer being characterized by the recurring unit:

(OC—R—NR'—X—NR'—R—COO—R'"—O)

where:
R is an aliphatic, aromatic or heterocyclic amino acid residue;
R' is H, alkyl (e.g. $C_1$ to $C_{10}$ alkyl) or a direct bond;
R" and R'" are the same or different aliphatic, aromatic or heterocyclic residue;
Z is C=O (amide); COO (urethane);

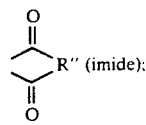
R" (imide);

CO—NR'(urea); or
=N (azo); and
X is an azo bond (N=N), urea or thiourea bond (NR'—CX'—NR' where X' is O or S.

It will be appreciated that polymers (a)-(c) are polyanhydrides while polymers (d)-(f) are polyesters. These polymers may be prepared in conventional manner using the indicated monomers, with or without co-monomers, to make homopolymers or copolymers. The polymers may serve either as carriers for a biologically active material or as the active agent itself depending on the composition involved.

DETAILED DESCRIPTION OF THE INVENTION

The invention contemplates the use of any available amino acid e.g. alanine, glycine or the like.

Typical coupling agents include any dicarboxylic acid or derivative thereof which forms a diacid with an amide bond in the backbone, any tetracarboxylic acid derivative which forms a diacid with an imide bond in the backbone, any diisocyanate which forms a diacid with a urea bond in the backbone, and any dichlorocarbonate which forms a diacid with a urethane bond in the backbone. As examples of such coupling agents there may be mentioned the following:

dicarboxylic acid derivatives sebacoyl chloride; adipoyl chloride; terephthaloyl chloride; methyl sebacate; methyl adipate; 1,4-cyclohexane-dicarboxylic acid; succinic, maleic, glutaric, citraconic and itaconic anhydrides: and fumaryl chloride.

tetracarboxylic acid derivatives 1,2,4,5-benzenetetracarboxylic anhydride; tetrahydrofuran-2,3,4,5-tetracarboxylic acid and 1,2,4,5-cyclohexanetetracarboxylic acid .

diisocyanates toluene diisocyanate; 1,6-diisocyanatehexane; 1,4-cyclohexane diisocyanate; and phenylene diisocyanate.

dichlorocarbonates phenylene dichlorocarbonates, hexane dichlorocarbonates, pentane dichloroformate and cyclohexanedichloroformate.

Representative illustrations of the coupling of amino acids with molecules having a carboxylic acid group include: amidation of amino acids with cyclic anhydrides, monosubstitution of dicarboxylic acid derivatives by an amide bond; tricarboxylic anhydrides forming an imide bond, or the like.

Direct coupling of two amino acids via the amino group to form a urea, thiourea or azo bond can be conducted by known methods. See, for example, *Advanced Organic Chemistry,* March J., editor, John Wiley & Sons 3rd edition 1985; coupling by urea or thiourea bond-Yamazaki N. Higashi F. and Iguchi T., Tetrahedron Letters 1974, 13, 1191; coupling by azo bond-Firouzabadi and Mostafavipoor, Bull. Chem. Soc. Jpn 1983 56, 914.

Dicarboxylic acids, prepared as generally described above, may be homo- or co-polymerized into polyanhydrides or polyesters using known polymerization methods, e.g., polyanhydrides may be prepared by melt or solution polymerization according to *Ency. of Poly. Sci. and Tech.,* Vol. 10, Wiley, N.Y., pps. 630–653; A. Domb and R. Langer, *J. Polym. Sci.,* 1987, 25, 3373; U.S. Pat. Nos. 4,757,128 and 4,789,724; A. Domb, E. Ron, and R. Langer, *Macromolecules,* 1988, 21, 1925; and pending U.S. Pat. application Ser. No. 07/080,332 while polyesters may be made as described in *Ency. of Poly. Sci. and Tech.,* Vol. 11, Wiley, N.Y., 1969.

The various aspects of the invention are illustrated in a non-limiting way by the detailed examples given later herein. In summary, these examples demonstrate the following:

A. Preparation of diacids from amino acids by 1 reaction between amino acids and cyclic anhydrides to form an amide or imide bond via the amino group. The cyclic anhydride may be a cyclic anhydride of a dicarboxylic acid, e.g. succinic, maleic or glutaric anhydride, or a cyclic anhydride of a tetracarboxylic acid derivative to form an imide bond, e.g. the anhydride or imide derivative of 1,2,4,5 benzenetetracarboxylic acid, and 2,3,4,5, tetrahydrofurantetracarboxylic acid;

2. mono or disubstitution of dicarboxylic acid derivatives with an amino acid via the amino group; or 3. coupling of amino acids by an azo bond via the amino group;

B. Polymerization of the resulting amide or imide containing dicarboxylic acids obtained as above may be accomplished by either:

(a) anhydride homopolymerization or copolymerization with aliphatic or aromatic diacids using, for example, melt or solution polymerization methods, or (b) ester condensation with a glycol to form a polyester.

It will be appreciated that the amino acid molecules that are used herein may be any molecule containing a carboxylic acid or its derivative and a primary or secondary amino group, including, natural and modified α-amino acids, polypeptides with carboxylic acid or its derivative and amino group terminals, γ-alkyl amino acids, and aromatic amino acid, e.g. amino benzoic acid derivatives.

Acid derivatives used herein include any aromatic, aliphatic or heterocyclic dicarboxylic acid derivative that forms an amide bond with the amino group, leaving intact the carboxylic acid of the amino acid. Examples are mono or dichloride derivatives of alkyl or aryl dicarboxylic acids, mono or dimethylester derivatives of alkyl or aryl dicarboxylic acids.

It will be appreciated that the polymers of the invention differ substantively from the case where, for example, polyesters are prepared by polymerizing hydroxy proline. See, J. Kohn and R. Langer, "Polymerization Reactions Involving the Side Chains of α-L-Amino Acids," *J. Am. Chem. Soc.,* 109:817 (1987). In such procedures, the polymerization proceeds through the carboxyl group and the hydroxy group of the amino acid, the amine group itself being protected from reaction. In the present case, the carboxylic acid group is introduced onto the amine nitrogen and the polymerization proceeds through this group so that the amine nitrogen is included in the polymer backbone rather than as a side chain.

The invention is illustrated by the following examples:

EXAMPLE 1

Preparation of dicarboxylic acids by the reaction of an amino acid and a cyclic anhydride Succinyl, maleic and glutaryl derivatives of amino acids were synthesized by the reaction of succinic, maleic or glutaric anhydride with various amino acids in an organic solvent, glacial acetic acid, pyridine or tetrahydrofuram (THF). The present example illustrates the reaction using succinyl, maleic and glutaryl derivatives in THF as follows:

0.1 mole of fine powdered amino acid was swirled in 100 ml refluxing tetrahydrofuran (THF). To the mixture was added dropwise over 10 min., 0.1 mole of succinic, maleic or glutaryl anhydride in 100 ml THF. After 5 hrs at reflux the solvent was evaporated to dryness, and the white product was recrystallized from ethanol-water or acetone-water solutions. The data analysis is summarized in Table 1.

TABLE 1

Data analysis of Amino acid succinamide derivatives

| Amino acid | Melt Point (°C.) | Yield (%) | Acid content found (mmol/g) | calculated (mmol/g) | Spectra analysis |
|---|---|---|---|---|---|
| DL-alanine | 173–5 | 90 | 10.65 | 10.58 | 6 |
| β-alanine | 168–71 | 86 | 10.63 | 10.58 | c |
| -amino-butyric acid | 110–12 | 85 | 9.88 | 9.85 | d |
| DL-phenyl-alanine | 144–6 | 90 | 7.60 | 7.55 | e |
| L-proline | <30 | 83 | 9.52 | 9.30 | f |
| p-amino benzoic acid | 253–5 | 94 | 8.51 | 8.43 | g |
| β-alanine[h] | 155–9 | 86 | 10.10 | 9.95 | h |
| p-amino benzoic acid[i] | 228–232 | 80 | 7.60 | 8.51 | i |

The acid content, IR (sharp peak at 3300–3500, characteristic for -N-H bond stretching) and $^1$H-nmr spectra analysis, confirm the formation of the diacid. The product was obtained in high purity and yield in a single step. Succinyl and glutaryl derivatives of amino acids are known for their biological activity as potent competitive inhibitors of Angiotensin-Converting Enzyme (Cushman D.W.; Chung, H.S.; Sabo, E.F. and Ondetti, M.A., Biochemistry, 16,5484, 1977). A number of N-dicarboxylmonoglycines are also of biological interest as metabolites in aciduias patients (Geregersen, N; Gron, I; Rasmussen, K; and Kolvraa S., Biomed. Mass Spec. 5, 80, 1978). Therefore polymers with hydrolytically labiled bonds made of these diacids could serve as degradable polymeric prodrugs.

EXAMPLE 2

Preparation of dicarboxylic acids from the reaction of amino acids and diacid chlorides The reaction of β-alanine with phthaloyl chloride is as follows:

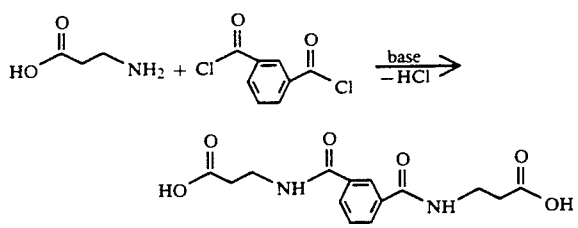

Diacid chloride (0.05 mole) dissolved in 80 ml dichloromethane, was added to a stirred solution of β-alanine (0.1 mole) and NaHCO$_3$ (0.1 mole) in 30 ml water at 0° C. After 1 hour the reaction mixture was allowed to come to room temperature and stirred for 5 hours. The dichloromethane was evaporated and the white precipitate was dissolved in 0.5N NaOH. The solution was filtered and acidified to yield after isolation and freeze drying, a white power. The data analysis is summarized in Table 2.

TABLE 2

Coupling of β-alanine with diacid chlorides

| Acid chloride | Melt Point (°C.) | Yield (%) | Acid content found calculated (mmole/g) | | IR (cm$^{-1}$, nujol) |
|---|---|---|---|---|---|
| Sebacoyl Cl. | 93.4 | 86 | 5.77 | 5.81 | 3280,1680 |
| Adipoyl Cl. | 54–6 | 82 | 6.91 | 6.94 | 3280,1690 |
| i-Phthaloyl Cl | 114–6 | 88 | 6.44 | 6.49 | 3280,1700,1610 |

*Determined by base titration.*

EXAMPLE 3

Preparation of N-dicarboxylmono-amino acids by monosubstitution of diacid chlorides with amino acids Sebacyl and adipyl mono glycine or β-alanine were prepared from the reaction of β-alanine or glycine with sebacoyl chloride or sebacylmonochloride, as follows:

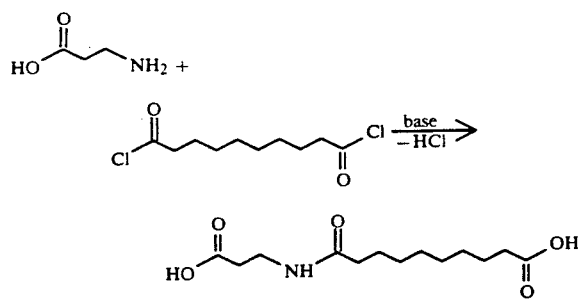

Sebacoyl chloride (0.1 mole) dissolved in 80 ml dichoromethane, was added at once to a stirred solution of β-alanine (0.1 mole) and NaHCO$_3$ (0.15 mole) in 60 ml water at 0° C. After 1 hour, the reaction mixture was allowed to come to room temperature and stirred for an additional 5 hours. The dichloromethane was evaporated and the pH of the aqueous medium was adjusted to 1. The white precipitate was isolated by filtration and freeze-dried. The product was recrystallized from ethyl acetate-petroleum ether to yield (55%) a white power. Data analysis: melting point, 124°-6° C., acid content, 7.4 mmole/g (calculated, 7.3 mmole/g) IR (cm$^{-1}$, nujo 10 3280, 1680.

Alternatively, N-dicarboxylmon-amino acids were prepared according to Geregersen (Geregersen, N.; Gron, I.; Rasmussen, K.; and Kolvraa S., Biomed. Mass Spec. 5,80, 1978).

The adipyl and sebacylglycines were synthesized as follows: Dicarboxylic acid (0.1 mole) was reacted with thionyl chloride (0.1 mole) in 100 ml refluxing dry dioxane for 5 hours. The dioxane was evaporated to dryness and the dicarboxylmonochloride was mixed with a solution of β-alanine or glycine (0.3 mole) and NaHCO$_3$ (0.15 mole) in 60.ml of water. After 5 hours at room temperature, the reaction mixture was saturated with NaCl and the pH was adjusted to 1. The precipitate was isolated by filtration and recrystallized from ethyl acetate-petroleum ether (yield 60%). Data analysis; adipylmonoglycine, MP 136°-140° C., acid content, 10.1 mmole/g (calculated, 9.9 mmole/g), IR (cm$^{-1}$, nujol) 3280, 1680. Sebacylmonoglycine, MP 122°-127° C., acid content, 7.4 mmole/g (calculated, 7.3 mmole/g), IR (cm$^{-1}$, nujol) 3280, 1680.

EXAMPLE 4

Coupling of amino acids using benzene tetracarboxylic anhydride (BTCA) as coupling agent The preferred method for synthesizing optically active imides of amino acids is that of Nefkens (Nefkens, H.G.L., Tesser, G.I., Nivard, R.J.F., Recveil, 79, 688 (1960). In the present example, a two-step method is used to form pyromellyl amine acid derivatives based on a method developed by Billman and Harting (Billman J.H. and Harting W.F., *J. Amer. Chem. Soc.*, 1948, 70, 1473) for the synthesis of phthalyl derivatives of amino acids. The method used was as follows:

(0.10 mole) BTCA dissolved in THF (20 ml) was added to a stirred refluxing mixture of amino acid (0.20 mole) in THF (50 ml). After 3 hours at reflux a powdery material precipitated. The precipitate was isolated by filtration and washed with diethyl ether, yield, 70-85%. IR spectra analysis (-N-H stretching at 3280 cm$^{-1}$ medium, single) and titration of the product revealed the formation of the tetraacid. The product was then heated at 180° C. under vacuum (0.1 mm Hg) for 30 min. The formation of the diimide was confirmed by IR (disappearance of the -N-H absorbance at 3300 cm$^{-1}$) and base titration. It appears that the imide bond probably hydrolyzed during titration. Nonaqueous titrations gave better results. The product of L-proline with a secondary amine formed the tetraacid and was not heated for the second step. The data analysis is summarized in Table 3.

TABLE 3

Data analysis of pyromellyl diamino acids

| Amino acid | Melt point (°C.) | Acid Content (mmole/g) found calculated | | yield (%) | IR (cm$^{-1}$, nujol) |
|---|---|---|---|---|---|
| β-alanine | 355 decomp. | 5.74 | 5.55 | 78 | 1700 |
| p-amino benzoic acid | >350 | 4.05 | 3.94 | 88 | 1690,1640,1600 |
| L-proline | 165 | 8.25 | 8.92 | 85 | 1710 |

TABLE 3-continued

Data analysis of pyromellyl diamino acids

| Amino acid | Melt point (°C.) | Acid Content (mmole/g) found calculated | yield (%) | IR (cm$^{-1}$, nujol) |
|---|---|---|---|---|
| | decomp. | | | |

Coupling of amino acids using 2,3,4,5, tetrahydrofuran-tetracarboxylic acid, as coupling agent was done similarly. The 2,3,4,5, tetrahydrofuran tetracarboxylic anhydride was prepared from the reaction of 2,3,4,5, tetrahydrofurantetracarboxylic acid in acetic anhydride. The diimide derivative of β-alanine was prepared. Data analysis: melting point, 284°-7° C., IR (cm-$^1$, nujol) 1720, 1630, 1530, acid content, 5.9 mmole/g (calculated, 5.6 mmole/g). The diacid was polymerized as follows:

Tetrahydrofuran tetracarboxylic acid diimide derivative (3g) was reacted with refluxing acetic anhydride (30 ml) for 30 min. The clear solution was concentrated to 5-8 ml by evaporation and left over night in a freezer. A white precipitate was obtained which was isolated by filtration and washed with diethyl ether (60% yield), melting point, 223°-7° C., IR (cm-$^1$, nujol), 1840, 1790 (broad). The prepolymer was polymerized at 180° C. for 30 min. under vacuum of 0.1 mm Hg. The polymer was brittle with a melting range of 255°-263° C., IR (cm-$^1$, film cast) 1810, 1740, 1700 (broad). Copolymerization with sebacic acid prepolymer (20:80 molar ratio) yielded a pliable polymer, melted at 52°-58° C. IR (cm-$^1$, film cast) 1820, 1750, 1700 (broad).

Polymerization

Polyanhydrides according to the invention may be synthesized using, for example, the melt or solution polymerization procedures described by A. Domb and R. Langer, in *J. Polym. Sci.*, 1987, 25, 3373; U.S. Pat. Nos. 4,757,128 and 4,789,724; A. Domb, E. Ron, and R. Langer, in *Macromolecules*, 1988, 21, 1925, and U.S. Pat. No. S.N. 080,332, the contents of these reference disclosures being incorporated herein by reference. Melt polymerization in general yields higher molecular weight polymers. However this type of polymerization involves the use of high temperatures which may decompose temperature sensitive monomers. When optical activity is important, e.g. in the preparation of polymeric amino acid prodrugs, solution polymerization is preferred. Solution polymerization may be conducted under mild conditions and may maintain the biological and optical activity of the monomeric drug. However, in general, high molecular weight polymer cannot be achieved by this method. The specific polymerization conditions will, therefore, normally be selected according to the polymer properties desired. Copolymerization with other monomer units may also be used to achieve desired overall properties.

The polymerization methods used for present purposes to make the anhydride polymers may be illustrated as follows:

Melt Polymerization:

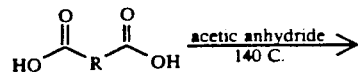

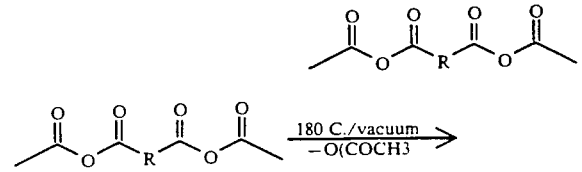

Solution Polymerization:

Coupling with Diacid Chloride:

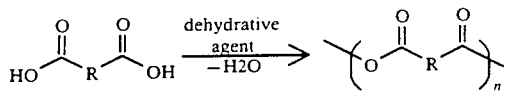

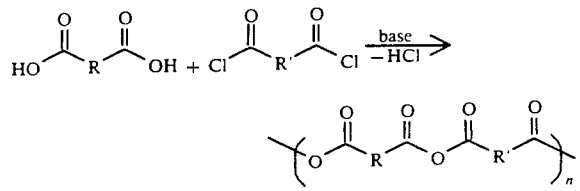

It will be recognized that the molecular weight of the polymers prepared according to the invention can be widely varied depending on the polymer composition, the manner in which it is to be used and other factors. Usually, however, the weight average molecular weight of the polymer will be at least about 1000 and usually greater than about 20,000 although polymers of lower weight average molecular weight are also contemplated as useful for present purposes.

The following examples more specifically illustrate the preparation of polymers according to the invention:

EXAMPLE 5

Melt polymerization

Mixed anhydride or acetic acid prepolymers were prepared either by refluxing the diacids in acetic anhydride or by the reaction with acetyl chloride in the presence of an acid acceptor under mild conditions. The second is preferable for the modified amino acids, because the reaction with acetic anhydride may form the azlactone (A.T. Balaban; J. Schikeetanz; M. D. Gheorhiu, and A. Schiketanz, *Revue Roumaine de Chimie*, 30, 977, 1985).

Prepolymers in acetic anhydride were prepared as follows:

Fine powder of the diacid (3.0 g) was added to refluxing acetic anhydride (30 ml). After 15 minutes of reflux the clear solution was evaporated to dryness, and the residue was purified by quenching in 9:1 v/v petroleum ether:diethyl ether mixture, from dichloromethane solution.

The formation of prepolymers by the reaction with acetyl chloride, was as follows:

Diacid monomer (0.1 mole) was dissolved in a solution of triethylamine (0.2 mole) in dichloromethane (200 ml). To the solution was added a solution of acetyl chloride (0.2 mole) in dichloromethane (50 ml). The reaction was maintained at 5° C. for 1 hour and 5 hours at room temperature. The precipitated amine-HCl complex was isolated by filtration and the filtrate was extracted with cold water, dried over magnesium sulfate and concentrated to about 50 ml by evaporation. The concentrated solution was poured in dry hexane to yield a precipitate. IR spectra analysis show characteristic absorbencies for anhydride and -N-H stretching bonds at 3340, 1810 and 1740 cm$^{-1}$.

Melt homopolymerization of the amino acid succinamide or glutarylamide derivatives yielded low molecular weight polymers (Mw=800-2000). It is likely that the low molecular weight is a result of side reactions, lactone formation [Crawford and Little, J. Chem. Soc. 722 and 729 (1959)] and/or internal imide cyclization, which terminate the polymerization. However, melt copolymerization with sebacic acid or isophthalic acid prepolymers yielded high molecular weight polymers.

The polymerization was performed as follows:

Mixtures of the prepolymer powders containing 80 molar % sebacic acid prepolymer or 50 molar %isophthalic acid prepolymer were placed in a Kimax tube with a side arm. The tube was placed in an oil bath at 180=1° C. Vacuum was applied through the side arm (100 micron Hg) and the polymerization was continued for 60 min. The viscous polymer was removed from the tube (85-95 % yield) and purified by quenching in petroleum ether from dichloromethane solution. The data analysis is shown in Table 4.

TABLE 4

Copolymers of sebacic acid or isophthalic acid and amino acid succinamide derivatives

| Amino acid | Melt point (°C.) | Molec weight Mw | | Viscosity (dl/g) |
|---|---|---|---|---|
| copolymers with sebacic acid (20:80 molar ratio) | | | | |
| β-alanine | 75-9 | 36900 | 11800 | 0.55 |
| DL-alanine | 74-9 | 34400 | 12600 | 0.53 |
| PABA | 64-69 | 24700 | 800 | 0.42 |
| GABA | 77-83 | 27500 | 8900 | 0.37 |
| PABA$^b$ | 58-64 | 20700 | 8200 | 0.40 |
| copolymers with isophthalic acid (50:50 molar ratio) | | | | |
| β-alanine | 84-9 | 6500 | 3400 | 0.15 |
| PABA | 82-8 | 8700 | 45000 | 0.21 |

$^a$molecular weights were determined by GPC, intrinsic viscosity was measured in dichloromethane at 25° C.
$^b$PABA derivative of maleic anhydride. IR (cm$^{-1}$, film), 3330, 3100, 1800, 1730, 1600, 1510 (all sharp peaks).

The copolymers of sebacic acid were pliable and formed a film from dichloromethane by solvent casting. Copolymers of isophthalic acid were brittle and glassy. IR spectra (film cast on NaCl pellets) showed absorbencies at 1810 and 1740 cm$^{-1}$ (sebacic acid copolymers) and 1790 and 1720 cm$^{-1}$, characteristic for anhydride bonds.

EXAMPLE 6

Solution copolymerization

This example illustrates solution copolymerization of amino acid-succinamide derivatives with diacid chlorides.

Fine powder of the amino acid-succinamide monomer (0.0mole) was stirred in dry dichloromethane (10 ml) containing 4-PVP(0.01 mole equivalent). To the mixture was added sebacoyl chloride (0.01 mole) in dichloromethane (5 ml). The reaction was stirred at 0° C. for 2 hours, then 3 hours at room temperature. The mixture was filtered and the filtrate was concentrated to 3-5 ml and quenched in 30 ml petroleum ether to yield (60-80%) of a white solid.

DL-alanine copolymer MP-79°-85° C., IR (film cast, cm$^{-1}$) 1810, 1740, 1690; Mw-4500. β-alanine copolymer MP-84°-90° C., IR (film cast, cm$^{-1}$) 1810, 1740, 1690; Mw-5500 DL-phenylalanine copolymer, MP-122°-126° C., IR (film cast, cm$^{-1}$) 1810, 1740, 1690; Mw-4200.

EXAMPLE 7

Melt homopolymerization of N,N'-bis(β-alanine) dicarboxamide

The dry powdered diacid (3g) was added to refluxing acetic anhydride (30 ml) and refluxed for 15 min. The clear solution was evaporated to dryness, and the prepolymer was purified by quenching in 9:1 v/v petroleum ether: diethyl ether mixture, from dichloromethane solution. IR spectra analysis show characteristic absorbencies for anhydride and -N-H stretching bonds at 3340, 1810 and 1740 cm$^{-1}$. The prepolymers were polymerized at 180° C. under 0.05 Hg vacuum for 60 min. The data analysis is summarized in Table 5.

TABLE 5

Polymerization of N,N'-bis(β-alanine) dicarboxamide

| Diacid | Melt point (°C.) | IR (cm$^{-1}$, nujol) | appearance |
|---|---|---|---|
| sebacoyl | 55-60 | 3320,1810,1740,1690 | rubbery |
| adipoyl | 81-86 | 3290,1790,1720,1640 | glassy, brittle |
| i-phthaloyl | 88-95 | 3300,1810,1720,1690, 1640, 1530 | glassy, brittle |

The polymers were soluble in DMSO, and possess fiber forming properties from the melt. Monosubstituted β-alanine-sebacic acid was polymerized similarly, to yield a pliable polymer, melted at 62°-66° C., IR (cm$^{-1}$, film) 3340, 1810, 1740, 1700.

EXAMPLE 8

Copolymerization

The N,N'-bis(β-alanine) dicarboxamide monomers were melt copolymerized with sebacic acid prepolymer 20:80 molar ratio. The polymers were soluble in CH$_2$Cl$_2$, pliable and possess film forming properties (solvent cast). The data analysis is summarized in Table 6.

TABLE 6

Copolymerization of diacid-di β-alanine with sebacic acid (20:80)

| Diacid | Melt point (°C.) | Molec. weight | | IR$^b$ (cm$^{-1}$, film cast) |
|---|---|---|---|---|
| | | Mw | Mn | |
| sebacoyl | 69-75 | 22400 | 8900 | 3300, 1810, 1740, 1700 |
| adipoyl | 45-52 | 18100 | 5850 | 3280, 1810, 1740, 1700 |
| i-phthaloyl | 55-60 | 26950 | 12100 | 3300, 1810, 1730, 1700 |

$^a$determined by GPC
$^b$characteristic for amide and anhydride bonds

EXAMPLE 9

One step polymerization

Carboxylic acids form anhydride bonds when reacted with acid chlorides in the presence of an acid acceptor. Under the same conditions amines react with acid chlorides to form amide bonds. Thus, reacting amino acids with diacid chlorides under anhydrous conditions, in the presence of an acid acceptor should yield a poly(amide-anhydride) in one step under mild conditions. This is believed to be useful, particularly towards the preparation of polymeric drugs of biologically active amino acids to be used as prodrugs.

The reaction for β-alanine and sebacoyl chloride is as follows:

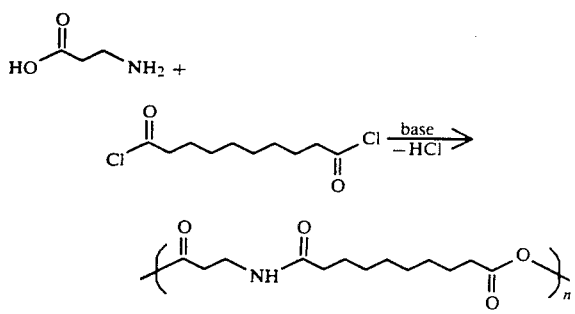

Procedure

Fine powder of amino acid (0.01 mole) was stirred in dichloromethane (10 ml) containing 4-PVP (0.01 mole amine groups). To the mixture was added dropwise over 10 min, diacid chloride (0.01 mole) in dichloromethane (5 ml). The reaction was stirred at 0° C. for 2 hours then 3 hours at room temperature. The mixture was filtered and the filtrate was concentrated to 3-5 ml and quenched in 30 ml petroleum ether, to yield (50-80%) of a white solid. The solid was washed with dry diethylether and dried in an anhydrous vacuum desiccator. The polymers had weight average molecular weights of 2100 and 4800. The data analysis is summarized in Table 7.

TABLE 7

| | | | |
|---|---|---|---|
| One step polymerization of amino acids and diacid chlorides | | | |
| Amino acid | Acid | Melt chloride point (°C.) | IR[a] (cm$^{-1}$, film cast) |
| β-alanine | sebacoyl | 57-63 | 3400,3300,1810,1740,1406 |
| β-alanine | adipoyl | 80-85 | 3410,1800,1740,1680 |
| DL-alanine | sebacoyl | 54-60 | 3400,1810,1730,1650 |
| L-proline | sebacoyl | 35 | 1810,1740,1700,1680 |

[a]characteristic for amide and anhydride bonds

EXAMPLE 10

Polymerization of Pyromellyl-amino acids, imide derivatives

The diacids described in Example 4 were homo-and copolymerized by melt condensation.

a. Preparation of poly(pyromellyl-di β-alanineimide). Pyromellyl-di β-alanine, imide derivative (3.0g) was added to refluxing acetic anhydride (30 ml) and reacted for 30 min, whereby a clear solution was obtained. The solution was left over night at room temperature. A yellowish powder precipitated out, and was isolated by filtration. The powder was washed with diethyl ether and dried in an anhydrous vacuum desiccator (80% yield). Data analysis: melting point, 320°-5° C. with decomposition. IR (cm-1, nujol) 1800, 1750, 1700; soluble in DMSO.

Melt polymerization-homopolymerization was not effective because of the high melting point of the prepolymer. Copolymerization with sebacic acid prepolymer (20:80 molar ratio) at 180° C. for 90 min under vacuum of 50 micron Hg, yielded a pliable material which possessed film-forming properties when solution cast, and fiber-forming properties when drawn from the melt. Both the films and fibers show high flexibility and relatively high mechanical strength. Analysis: melting point, 80-6° C.; IR (cm-1, film cast) 1800, 1740, 1720; molecular weight (GPC) Mw-26810, Mn-19050.

b. Preparation of poly (pyromellyl-di-PABA imide). Pyromellyl-di PABA imide derivative (3.0 g) was added to refluxing acetic anhydride (30 ml) and reacted for 5 hours. The solid was isolated by filtration and washed with diethyl ether. Analysis: melting point, 350° C, IR (cm-1, nujol) 1825, 1780, 1720;

Copolymerization with sebacic acid prepolymer (20:80 molar ratio) at 180° C. for 90 minutes under vacuum of 50 micron Hg, yielded a pliable material. Analysis: melting point, 80-6° C.; IR (cm-1, film Cast) 1800, 1740, 1720; molecular weight (GPC) Mw-22500, Mn-8600.

c. Preparation of poly (pyromellyl-di L-proline imide). Pyromellyl-di-L-proline, imide derivative (3.0 G) was added to refluxing acetic anhydride (30 ml). Immediately after addition the solid mixture turned brown. The reaction was continued for 30 min, filtered and concentrated by evaporation to 5-8 ml. The viscous residue was poured into 50 ml of diethyl ether, to yield (75%) a gray powder. The powder was dissolved in dichloromethane, decolorized with active carbon, and quenched in petroleum ether. Data analysis: melting point, 225°-30° C. IR (cm-1, nujol) 1850, 1780, 1710, 1630;

Polymerization: homopolymerization at 180° C. for 20 min under vacuum of 50 micron Hg, yielded a dark polymer which melted at 158°-165° C., and decomposed at 235°-40° C. The polymer was soluble in dichloromethane. IR (cm-1, film cast) 1850, 1780, 1720, 1630; molecular weight (GPC) Mw-6400, Mn-3600. Copolymerization with sebacic acid prepolymer (20:80 molar ratio) at 180° C. for 30 min under vacuum of 50 micron Hg, yielded a pliable material. Analysis: melting point, 74°-9° C.; IR (cm-1, film cast) 1810, 1740; molecular weight (GPC) Mw-12400, Mn-5600.

EXAMPLE 11 polyanhydrides of 4,4'-Dihydroxyazobenzene-3.3-dicarboxylic acid 4,4'-Dihydroxyazobenzene-3,3'-dicarboxylic acid is clinically used as a prodrug for amino salicilic acid (Design of Prodrugs, Bundgaard H. editor, Elsevier Sci. Pub., Amsterdam, 1985, pp. 42). The azo bond is fast hydrolytically degraded at pH 7 to the respective amino acids. This is an example of an amino drug incorporated into a polyanhydride to form a poly (azoanhydride).

Preparation of polymers a. Solution polymerization:

A solution of sebacoyl chloride in dry dichloromethane (0.1066 ml, 0.5 mmol, in 1 ml) was added to a stirred mixture of 4,4'-dihydroxyazobenzene-3,3'-dicarboxylic acid disodium salt (0.173g, 0.5 mmol) in dichloromethane (1 ml), at 0° C. After 2 hours the reaction was allowed to come to room temperature and stirred for an additional 5 hours. The reaction mixture was filtered and the filtrate was quenched in petroleum ether to yield (30%) a yellow solid. IR spectra showed characteristic peaks for anhydride bonds at 1810, 1770, and 1740 cm-1. Similar results were obtained with adipoyl chloride. Addition of NaHCO3 to the reaction mixture gave similar results.

b. Melt polymerization:

4,4′-Dihydroxyazobenzene-3,3′-dicarboxylic acid (0.346g, 1.0 mmol) was added to refluxing acetic anhydride (1 ml). After 1 hour at reflux excess acetic anhydride was evaporated and sebacic acid prepolymer (80 or 90 molar %) was added. The mixture was polymerized at 180° C. for 90 min under vacuum of 100 micron Hg. Both copolymers were yellow and pliable. The polymers had an intrinsic viscosity of 0.24 (10:90) and 0.18 dl/g (20:80), when measured in dichloromethane at 25.C. DSC analysis showed a single sharp peak at 81° C, onset at 74.8° C., for the 10:90 copolymer, and peak at 87.3.C, onset at 80.7° C., for the 20:80 copolymer. IR (cm-1, film cast) 1810, 1740, characteristic for anhydride bonds.

EXAMPLE 12

Hydrolytic Degradation and drug release

The degradation of the present polymers occurs either by hydrolytic degradation, mainly of the anhydride bonds and/or by enzymatic degradation of the amide or imide bonds, to release the respective free amino acids as degradation products. In the following example, hydrolytic degradation and drug release using p-nitroaniline as a model drug are demonstrated. Compression molded discs (200 mg, d=1.4 cm) of polymers containing 5% w/w p-nitroaniline were placed in 200 ml isotonic buffer solution pH 7.4, at 37° C. Solutions were changed periodically and analyzed for degradation products by UV absorbance. Degradation products were monitored at 230 nm, and p-nitroaniline at 380 nm. The results are summarized in Table 8. The polymers studied were aliphatic polyanhydrides with water soluble degradation products; therefore short degradation times were expected (K.W. Leong, B.C. Brott and R. Langer, J. Biom. Mat. Res. 1985, 19, 941).

TABLE 8
Drug release and hydrolytic degradation of polymers a

| Polymer | hydrolytic degradation | | p-nitroaniline release | |
|---|---|---|---|---|
|  | t½ (days) | Degradation Time (days) | t½ (days) | release time (days) |
| b | 5 | 13 | 3 | 8 |
| c | 7 | 16 | 4 | 10 |
| d | 6 | 14 | 3 | 8 |
| e | 2 | 5 | 1 | 2 |
| f | 3 | 8 | 2 | 5 | a t½ is the time for 50% degradation or dry release and degradation time is for 95% degradation or dry release.
b copolymer of N,N′-bis (β-alanine) isophthaloylamide and sebacic acid, 20:80 molar ratio.
c copolymer of N,N′-bis(β-alanine) sebacoylamide and sebacic acid, 20:80 molar ratio.
d copolymer of β-alanine-succinamide and sebacic acid, 20:80 molar ratio.
e N,N′-bis(β-alanine) iso-phthaloylamide homopolymer
f N,N′-bis (β-alanine) adipoylamide homopolymer.

Examples 13 and 14 demonstrate the preparation of polyesters according to the invention:

EXAMPLE 13

Biodegradable polyesters based on the modified amino acids

The diacids described in Examples 1–4 were used for the synthesis of polyesters. Methods for the synthesis of polyesters are well established and described in textbooks and scientific reviews (Polyesters in Ency of Polym Sci, Tech, Vol. 11, Wiley N.Y. 1969). In this example polyesters were prepared by melt condensation of the methyl ester derivative of the diacids and glycols with acid catalysis. Polymers of one mixture of two or more diacids with various dialcohols can be prepared which may be present a whole range of physical and mechanical properties. Copolymerization with lactic and gylcolic acids was conducted to obtain improved degradable polymers for medical applications.

The following illustrates the polyesterification of β-alanine succinamide and propylene glycol:

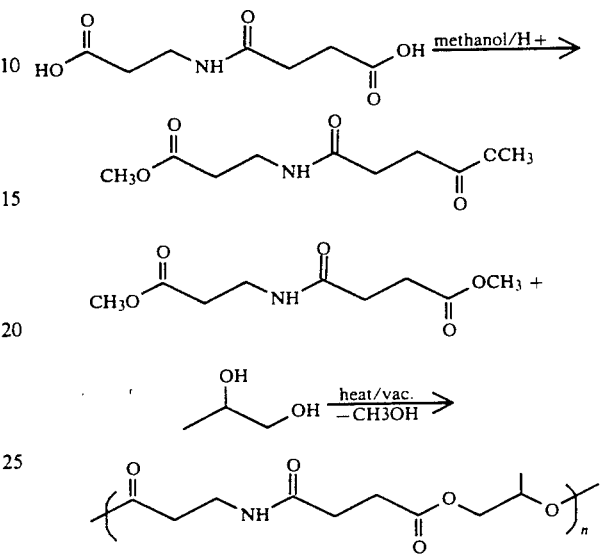

Procedure

Methyl esters were prepared by refluxing the diacid in excess methanol containing 0.1% $H_2SO_4$ as catalyst. IR showed an absorbencies at 1730 cm$^{-1}$, and no acid content by base titration.

The methyl ester (10 mmol) was mixed with propylene glycol (11 mmol) and p-toluene sulfonic acid (0.2 mmol), in a Kimax tube with a side arm. The tube was placed in an oil bath at 140° C. for 3 hours, then low vacuum (15 mm Hg) was applied through the side arm, and polymerization continued for an additional 3 hours. The temperature was raised to 180° C. and high vacuum (0.1 mm Hg) Was applied for 2 hours. The pliable transparent polymers were purified by quenching in hexane from dichloromethane solution. The polymer of β-alanine succinamide, had a molecular weight of 28,000, and melted at 66°–72° C. IR spectrum (film cast on NaCI pellets) was 3440 (N-H stretching, single, weak), 1730 (ester C=O, single, strong), and b 1690 cm$^{-1}$ (amide C=O, single, medium). The polymer of -amino butyric-succinamide had a molecular weight of 24,000, and melted at 62°–70° C. IR spectrum was 3440 (N-H stretching, single, weak), 1730 (ester C=O, single, strong), and 1635 cm$^{-1}$ (amide C=O, single, medium). The polymer of L-proline succinamide had a molecular weight of 33,000, and melted at 63°–70° C. IR spectrum was 1730 (ester C=O, single, strong), and 1635 cm$_{-1}$ (amide C=O, single, medium).

EXAMPLE 14

Biodegradable polyesters of DL-lactide and the modified amino acids

Polylactide and copolymers of lactide and glycoside are used as surgical sutures, surgical goods and as biodegradable carriers for controlled release applications (Craig P.H. et al, Surgery, 141, 1, 1975; Fong J. W. et al. in Controlled Release Technology Lee, P. I. and Good W.R. ACS symp. 348, Washington DC 1987). Copolymers of lactide and L-proline succinamide-propylene glycol were synthesized as follows:

Methyl ester of L-proline succinamide (10 mmol) was mixed with propylene glycol (11 mmol), DL-lactide (10 mmol), and stannous octoate (0.5 ml of 0.1M solution in dichloromethane), in a Kimax tube with a side arm. The tube was placed in an oil bath at 110° C. for 3 hours, then low vacuum (15 mm Hg) was applied through the side arm, and polymerization continued for additional 3 hours at 140° C. The temperature was raised to 180° C. and high vacuum (0.1 mm Hg) was applied for 2 hours. The pliable transparent polymers were purified by quenching in hexane from dichloromethane solution. The polymer had an intrinsic viscosity, [n]=0.53 dl/g and melted at 76°-82° C. IR spectrum (film cast on NaCl pellets) was, 1735 (ester C=O, single, strong), and 1635 cm-$^1$ (amide C=O, single, medium).

It is noted in connection with the preceding examples that the following instrumentation and methods were used for the indicated test purposes:

Infrared spectroscopy was performed on commercial available spectrophotometer. Polymeric samples were film cast onto NaCl plates from a solution of the polymer in chloroform. Acids and prepolymer samples were either pressed into KBr pellets or dispersed in nujol onto NaCl plates. The melting points of acids and prepolymers were determined on a digital melting point apparatus. Thermal properties of polymers was determined by a differential scanning calorimeter using a heating rate of 10° C./min. The molecular weight of the polymers was estimated on a Waters GPC system consisting of a Waters 510 pump and Waters programmable multiwavelength detector at 254 nm wavelength. Samples were eluted in dichloromethane through two Styrogel columns in series at a flow rate of 1.0 mL/min. Molecular weights of polymers were determined relative to polystyrene standards using Maxima 820 computer programs. Viscosity of polymers were determined on a conventional viscosimeter at 25° C. NMR spectra were obtained on a spectrophotometer using dimethyl sulfoxide-d6 (DMSO) and deuterium oxide containing NaOD as solvents for acids and chloroformdl containing tetramethylsilane (TMS) as solvents for polymers and prepolymers. UV absorbencies were determined on a Lambda 3B spectrophotometer. Acid content was determined by titration of solutions of acids in acetone or DMSO, with 0.1N NaOH standard solution to the end point of phenol phthalein. Degradation studies were performed at 37° C., using compression molded discs of 200 mg polymer containing 5% w/w p-nitroaniline, placed in 200 ml solution of phosphate buffer pH 7.40. Drug release and degradation rates were determined from the UV absorption of the degradation products in the degradation solution.

To summarize, the invention provides novel biodegradable polyanhydride and polyester polymer compositions based on amino acids. The polymers may be homopolymers or copolymers with other non-toxic comonomers. These polymers may be used as carriers for drugs or other biologically active agents intended for controlled release in the body. They may also be based on biologically active amino acids so that they function as both the carrier and source of the agent to be released.

The polymers are characterized by their physical and mechanical properties which result at least in part from the incorporation of bonds (amide, imide, urethane, urea or thiourea) with high cohesion energy. The polymers demonstrate outstanding surface erosion and drug release properties which make them suitable for use in controlled release compositions.

It will be appreciated that various modifications may be made in the invention as described above. Hence the scope of the invention is defined in the following claims wherein:

What is claimed is:

1. A biodegradable polyanhydride or polyester polymer selected from the group consisting of:

(a) polymers of at least one dicarboxylic acid made by coupling an amino acid with another molecule having a carboxylic acid group, said polymer including the repeating unit:

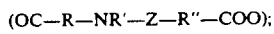
    (OC—R—NR'—Z—R"—COO);

(b) polymers of at least one dicarboxylic acid made by coupling two amino acids using a coupling agent, said polymer including the repeating unit:

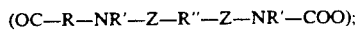
    (OC—R—NR'—Z—R"—Z—NR'—COO);

(c) polymers of at least one dicarboxylic acid made by direct coupling of two amino acids by an azo or urea bond, said polymer including the repeating unit:

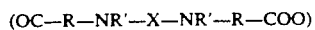
    (OC—R—NR'—X—NR'—R—COO)

d. Polymers of at least one dicarboxylic acid made by coupling an amino acid with another molecule having a carboxylic acid group, and at least one glycol, the polymer being characterized by the repeating unit:

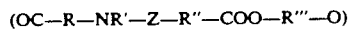
    (OC—R—NR'—Z—R"—COO—R'''—O)

e. Polymers of at least one diacid made by coupling of two amino acids using a coupling agent, and at least one glycol, the polymer being characterized by the repeating unit:

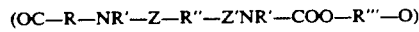
    (OC—R—NR'—Z—R"—Z'NR'—COO—R'''—O)

and, f. Polymers of at least one diacid made by direct coupling of two amino acids, by an azo, urea or thiourea bond, and at least one glycol, the polymer being characterized by the repeating unit:

    (OC—R—NR'—X—NR'—R—COO—R'''—O)

wherein

R is an aliphatic, aromatic or heterocyclic amino acid residue;

R' is hydrogen, alkyl or a direct bond;

R" and R''' are the same or different aliphatic, aromatic or heterocyclic residues;

Z is an amido, urethane, imido, azo, urea or thiourea linkage; and

X is an azo, urea or thiourea bond, provided that in the case of polymers (a), Z has a value other than imido.

2. A polyanhydride (a), (b) or (c) according to claim 1.

3. A polyester (d), (e), or (f) according to claim 1.

4. A homopolymer according to claim 1.

5. A copolymer according to claim 1.

6. A process for preparing a biodegradable polymer selected from the group consisting of:

(a) polymers of at least one dicarboxylic acid made by coupling an amino acid with another molecule having a carboxylic acid group, said polymer including the repeating unit:

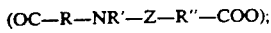
(OC—R—NR'—Z—R"—COO);

(b) polymers of at least one dicarboxylic acid made by coupling two amino acids using a coupling agent, said polymer including the repeating unit:

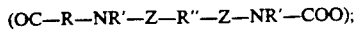
(OC—R—NR'—Z—R"—Z—NR'—COO);

(c) polymers of at least one dicarboxylic acid made by direct coupling of two amino acids by an azo or urea bond, said polymer including the repeating unit:

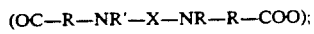
(OC—R—NR'—X—NR—R—COO);

(d) polymers of at least one dicarboxylic acid made by coupling an amino acid with another molecule having a carboxylic acid group, and at least one glycol, the polymer being characterized by the repeating unit:

(OC—R—NR'—Z—R"—COO—R'"—O);

(e) polymers of at least one diacid made by coupling of two amino acids using a coupling agent, and at least one glycol, the polymer being characterized by the repeating unit:

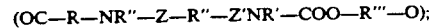
(OC—R—NR"—Z—R"—Z'NR'—COO—R'"—O);

and (f) polymers of at least one diacid made by direct coupling of two amino acids, by an azo, urea or thiourea bond, at least one glycol, the polymer being characterized by the repeating unit:

(OC—R—NR'—X—NR'—R—COO—R'"—O)

wherein

R is an aliphatic, aromatic or heterocyclic amino acid residue;

R' is hydrogen, alkyl or a direct bond;

R" and R'" are the same or different aliphatic, aromatic or heterocyclic residues;

Z is an amido, urethane, imido, azo, urea or thiourea linkage; and

X is an azo, urea or thiourea bond which comprises modifying an amino acid to include an additional carboxylic group therein and thereafter polymerizing the thus modified amino acid, provided that in the case of polymers (a), Z has a value other than imido.

7. The process of claim 6 wherein the modified amino acid is polymerized by a hydrolytically labile anhydride bond.

8. The process of claim 6 wherein the amino acid is modified by coupling with another molecule having a carboxylic acid group.

9. The process of claim 6 where the amino acid is modified by coupling together two amino acids through a coupling agent.

10. The process claim 6 wherein the amino acid is modified by coupling two amino acids by an azo, urea or thiourea bond.

11. A biodegradable polymer composition comprising a biologically active agent carried by a polymer according to claim 1.

12. A biodegradable polymer according to claim 1, wherein the polymer or a degradation product thereof is a drug or other biologically active agent.

13. A biodegradable polymer according to claim 1 wherein R is an alkylene group, R' is hydrogen, Z is an amido, urethane, imido, azo, urea or thiourea linkage; R" and R'" are the same or different and are selected from the group consisting of alkylene and phenyl and X is an azo, urea or thiourea group.

14. A biodegradable polymer according to claim 1 selected from polymers of a dicarboxylic acid made by coupling an amino acid with:

(1) a carboxylic acid derivative selected from the group consisting of sebacoyl chloride; adipoyl chloride phthaloyl chloride; terephthaloyl chloride; methyl sebacate; methyl adipate; 1,4-cyclohexane-dicarboxylic acid; succinic, maleic, glutaric, citraconic and itaconic anhydrides; fumaryl chloride;

(2) a tetracarboxylic acid derivative selected from the group consisting of 1,2,4,5,-benzenetetracarboxylic anhydride; tetrahydrofuran-2,3,4,5-tetracarboxylic acid and 1,2,4,5-cyclohexanetetracarboxylic acid;

(3) a diisocyanate selected from the group consisting of toluene diisocyanate; 1,6-diisocyanatehexane; 1,4-cyclohexane diisocyanate; and phenylene diisocyanate; and (4) a dichlorocarbonate selected from the group consisting of phenylene dichlorocarbonates, hexane dichlorocarbonates, pentane dichloroformate and cyclohexanedichloroformate.

15. A polymer according to claim 14 wherein the amino acid is alanine, glycine, amino butyric acid, phenylalanine, proline or amino-benzoic acid.

16. A polymer according to claim 15, said polymer being obtained by polymerizing the dicarboxylic acid reaction product of alanine and succinyl, maleic or glutaryl anhydride.

17. A controlled release composition comprising a biologically active component with a biodegradable polyanhydride or polyester selected from the group consisting of:

(a) polymers of at least one dicarboxylic acid made by coupling an amino acid with another molecule having a carboxylic acid group, said polymer including the repeating unit:

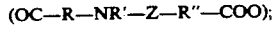
(OC—R—NR'—Z—R"—COO);

(b) polymers of at least one dicarboxylic acid made by coupling two amino acids using a coupling agent, said polymer including the repeating unit:

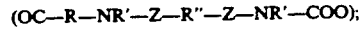
(OC—R—NR'—Z—R"—Z—NR'—COO);

(c) polymers of at least one dicarboxylic acid made by direct coupling of two amino acids by an azo or urea bond, said polymer including the repeating unit:

(OC—R—NR'—X—NR'—R—COO)

d. Polymers of at least one dicarboxylic acid made by coupling an amino acid with another molecule having a carboxylic acid group, and at least one glycol, the polymer being characterized by the repeating unit:

(OC—R—NR'—Z—R"—COO—R'"—O)

e. Polymers of at least one diacid made by coupling of two amino acids using a coupling agent, and at least one glycol, the polymer being characterized by the repeating unit:

(OC—R—NR'—Z—R"—Z'NR'—COO—R'"—O)

and, f. Polymers of at least one diacid made by direct coupling of two amino acids, by an azo, urea or thiourea bond, and at least one glycol, the polymer being characterized by the repeating unit:

(OC—R—NR'—X—NR'—R—COO—R'"—O)

wherein

R is an aliphatic, aromatic or heterocyclic amino acid residue;

R' is hydrogen, alkyl or a direct bond;

R" and R'" are the same or different aliphatic, aromatic or heterocyclic residues;

Z is an amido, urethane, imido, azo, urea or thiourea linkage; and

X is an azo, urea or thiourea bond.

18. A composition according to claim 17 wherein the biologically active component is a part of the biodegradable polyanhydride or polyester.

19. In a method of administering a biologically active agent by controlled release, the improvement which comprises utilizing a controlled release composition according to claim 17.

* * * * *